United States Patent [19]

Olson et al.

[11] 4,262,247
[45] Apr. 14, 1981

[54] MAKING AND USING CORROSION MEASURING PROBES FOR FLUID CONVEYING CONDUITS

[75] Inventors: Eugene E. Olson; Edwin T. Chiles; Alvin D. Goolsby, all of Houston, Tex.

[73] Assignee: Shell Oil Company, Houston, Tex.

[21] Appl. No.: 70,218

[22] Filed: Aug. 27, 1979

[51] Int. Cl.³ ............................................. G01R 27/02
[52] U.S. Cl. ............................... 324/65 CR; 324/71 R
[58] Field of Search ........................ 324/65 CR, 71 R; 73/61.2, 83; 23/230 C; 204/195 C; 422/53

[56] References Cited

U.S. PATENT DOCUMENTS

| | | | |
|---|---|---|---|
| 2,351,644 | 6/1944 | Talley et al. | 422/53 |
| 2,695,219 | 11/1954 | Upham | 73/86 X |
| 3,104,355 | 9/1963 | Holmes et al. | 324/71 R |
| 3,108,242 | 10/1963 | Scott, Jr. | 324/65 CR |
| 3,124,771 | 3/1964 | Rohrback | 324/65 CR |
| 3,936,737 | 2/1976 | Jefferies, Sr. | 324/65 CR |
| 4,019,133 | 4/1977 | Manley et al. | 324/71 R X |

*Primary Examiner*—Stanley T. Krawczewicz

[57] ABSTRACT

The corrosion of a fluid-conveying metallic conduit is measured by electrically connecting relatively thick and thin walled sections of that conduit as the arms of an electrical resistance-measuring bridge.

7 Claims, 4 Drawing Figures

MAKING AND USING CORROSION MEASURING PROBES FOR FLUID CONVEYING CONDUITS

BACKGROUND OF THE INVENTION

Known procedures for measuring corrosion have utilized measurements of the electrical conductivity and/or resistance of samples or probes inserted within the corrosive medium. For example, U.S. Pat. No. 3,104,355 describes use of a pair of relatively thick and thin corrodible metals connected as the legs of a balanced bridge circuit. Since corrosion changes the resistance of the thin element more than that of the thick element, the rate of corrosion is proportionate to changes in the ratio of their resistances. U.S. Pat. No. 3,108,242 describes probes which have relatively large surface areas. Such probes can be coated with a protective material such as paint and used in similar resistance measurements to determine the protective capability of the coating. That patent mentions numerous problems that may be encountered due to a change in the size and shape of such probes. U.S. Pat. No. 3,124,771 describes probes assemblies which can be supported within a fluid-conveying tube and used in similar measurements. Those probes are formed by mounting very thin shim stock on an electrical insulating material in order to obtain a probe which is mechanically strong but has a high sensitivity to corrosion.

SUMMARY OF THE INVENTION

The present invention relates to making and using probes for measuring corrosion of a metallic conduit which is conveying or is surrounded by a corrosive fluid. A section of the conduit is made or modified to form a measuring section. Within the measuring section, the wall portions which are contacted by the corrosive fluid have both compositions and configurations which are substantially the same as those which typify the remainder of the conduit. But, in locations within the measuring section in which the wall surfaces are not contacted by the corrosive fluid, the thickness of the metal in one portion is made thin relative to that in another. Those relatively thick and thin portions are electrically connected as the arms of an electrical resistance measuring bridge. And, preferably, corrosion rate measurements are made, by means of at least two time-separated measurements of the resistance ratio, while the measuring section is a part of the conduit and the conduit is being employed in its intended fluid-conveying operation.

DESCRIPTION OF THE INVENTION

Figure 1:
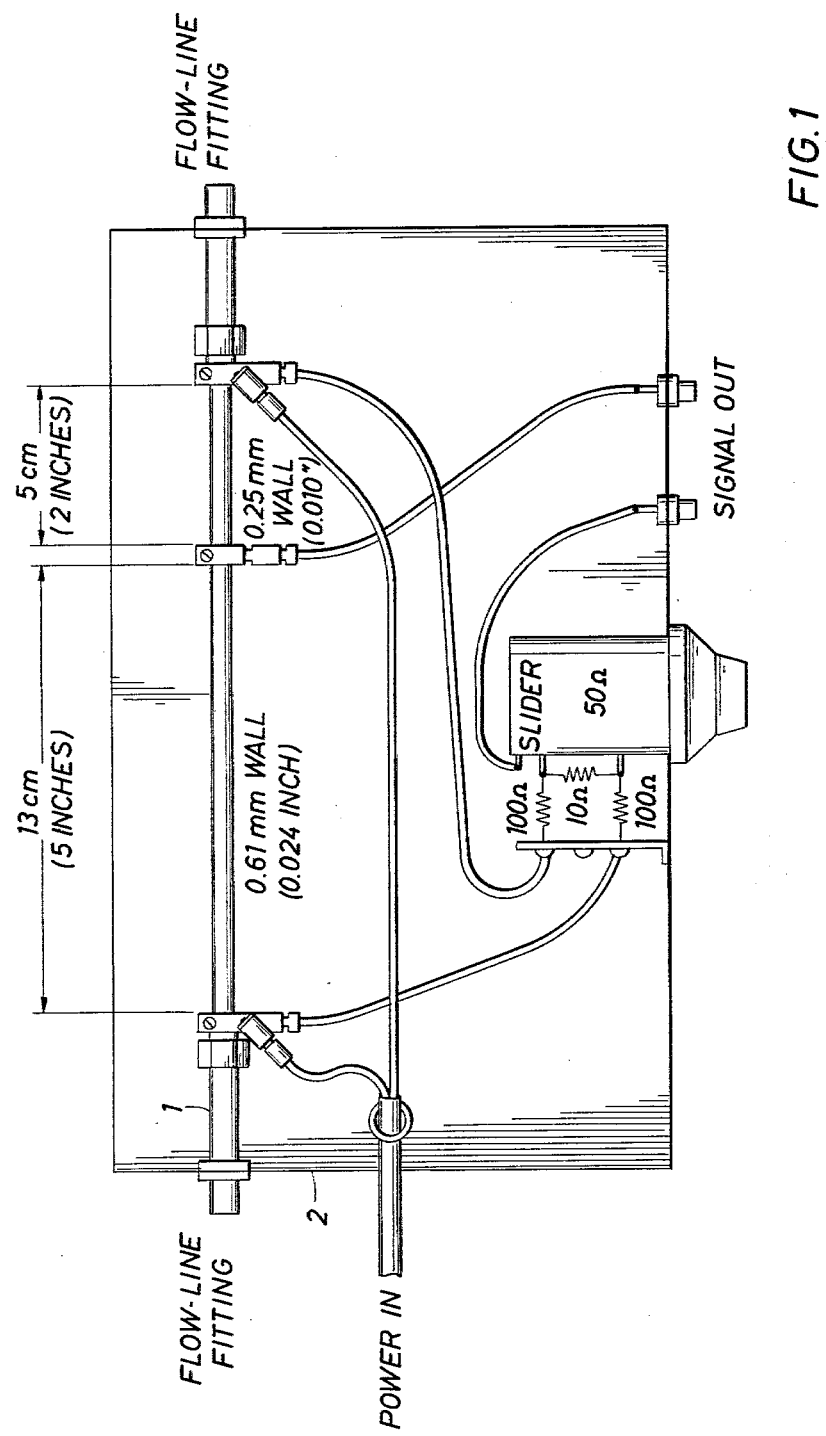
FIG. 1 schematically illustrates one preferred embodiment of the present probe.

FIG. 1 shows a particularly suitable embodiment of a steel pipe corrosion measuring probe of the present type. The probe element 1 comprises a section of tubing obtained from Kilsby Tube Supply of Houston. It has a nominal ¼-inch outer diameter by 0.022 inch wall (0.024 inch wall as received) fabricated of C1018 steel (carbon content 0.15 to 0.20%, magnesium content 0.6 to 0.9%, phosphorous content maximum 0.04% and sulphur content maximum 0.05%). The tubing was used essentially as received except for the machining of its outer walls to provide the illustrated 0.024 inch and 0.010 inch relatively thick and thin sections. The tube was provided with the illustrated electrical connecting elements and mounted within an aluminum box 2. The electrical connections to the tube were made with drilled and split copper blocks locked in place by clamping screws and the electrical leads were plugged into all-metal receptacles soldered to the copper blocks. A direct soldering of the electrical leads to such tubes has been found to be the preferred arrangement. The illustrated relatively thick and thin sections, fixed resistors and potentiometer form the legs of a resistance-measuring bridge, as shown in FIG. 2.

Figure 2:
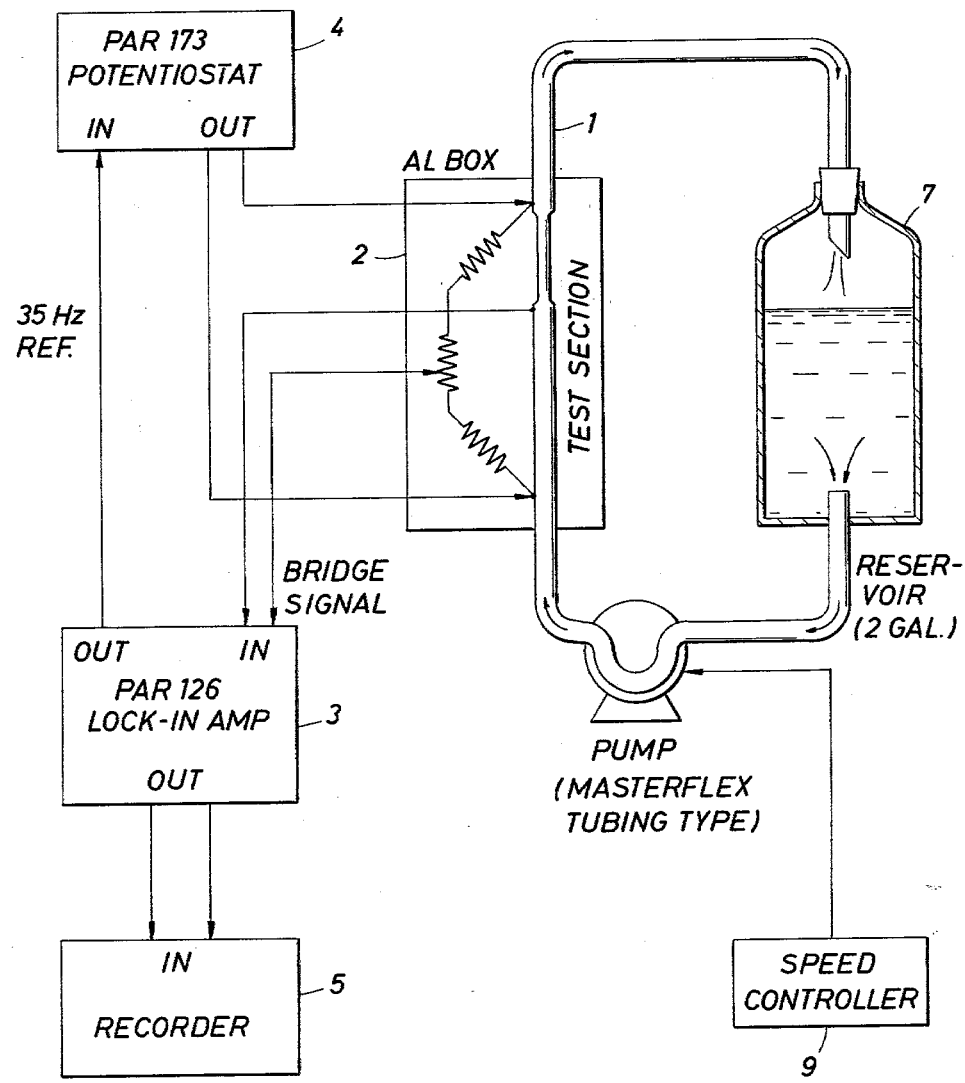
FIG. 2 is a block diagram of an arrangement for testing a probe of the present type.

FIG. 2 shows the principal components and electrical equipment used in laboratory tests of probes of the present type. The lock-in amplifier 3 is a Princeton Applied Research (PAR) Model 126 amplifier combined with a Model 116 differential pre-amplifier. Such an arrangement provides sufficient sensitivity and background rejection (through frequency and phase locking) for the low level signals encountered and also provides a stable adjustable reference frequency for the bridge exciter. The Potentiostat 4 for that exciter is a PAR Model 173 galvanostat with a Model 176 current follower. The recorder 5 is a Hewlett-Packard Model 7100BM strip chart recorder. The amplifier 3 and potentiostat 4 are powered from a Sola Model 23-22-125 constant voltage transformer (not shown). The tests were conducted with an operating frequency of 35 Hz.

In selecting the frequency to be used, it is preferable that the choice be compatible with factors such as the following: (1) harmonics of 60 Hz be avoided; (2) the best performance of a pre-amplifier such as the PAR 116 in the transformer mode is usually obtained at frequencies above about 10 or 20 Hz; but, (3) because of the skin-effect of an alternating current in an electrical conductor, it is desirable to use the lowest reasonable frequency.

In the lock-in amplifier 3 the reference channel output is preferably set to drive the galvanostat or potentiostat at 35 Hz. and a maximum current capability of about 0.6 amps rms. The galvanostat output is wired in series with the tubular probe element 1 so that most of the current goes through it with only a small fraction going through the fixed light resistors.

In operating the system, the bridge is, initially, deliberately unbalanced and the phase-angle for the lock-in amplifier is preferably set for the maximum angle. The bridge is then balanced by adjusting the potentiometer with the sensitivity being gradually increased to the desired level. A typical setting of 10 millivolts corresponds to a full scale sensitivity of plus or minus 1 microvolt on the panel meter, or strip-chart recorder. An appropriate time constant setting of from about 1 to 300 seconds is selected in order to eliminate excessive wander in the signal.

HYDRODYNAMIC EFFECTS OF CORROSION

Figure 3:
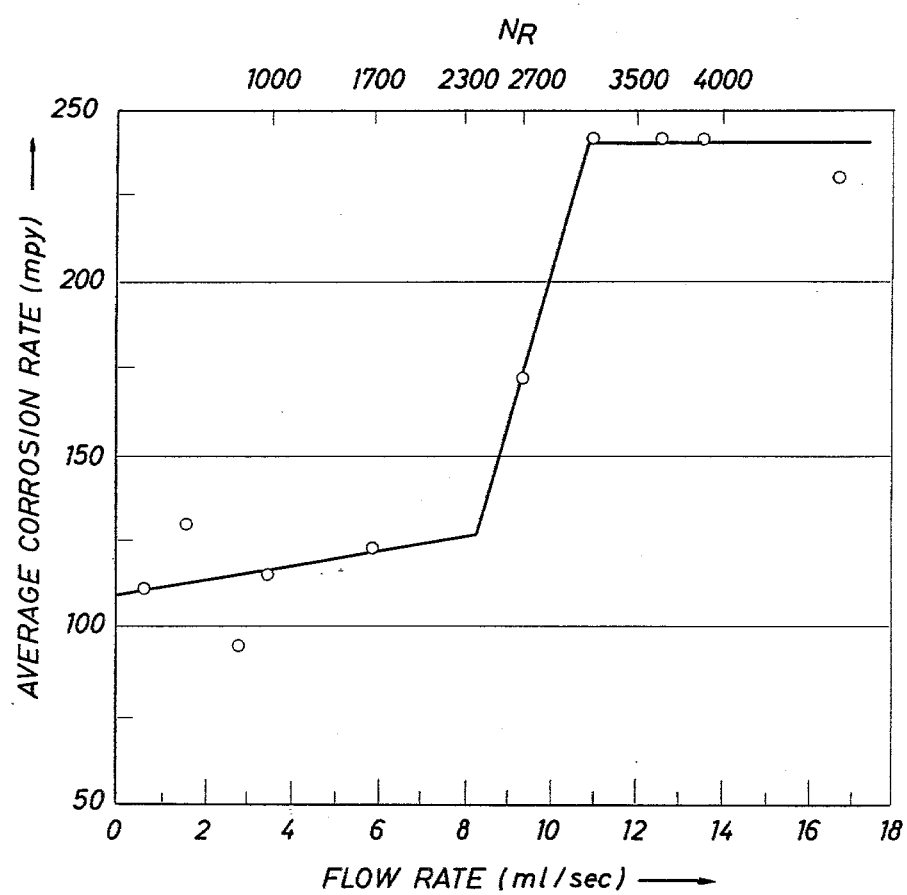
FIG. 3 shows a graph of the variation of an average corrosion rate with variation in flow rate.

Experiments were conducted to determine the ability of the present type of tubular corrosion measuring conduits to model the mass transport phenomenon as it affects corrosion within a pipeline. A 0.02% by volume hydrochloric acid solution was pumped through the apparatus of FIG. 2 at different rates of flow. The results are shown in FIG. 3, in terms of the average corrosion rate in mils per year (i.e, the number of thousandths of an inch lost per year) with increases in flow rate in milliliters per second. As shown in FIG. 3, a large stepwise reduction in corrosion rate occurred when the flow rate dropped from the turbulent region to the laminar region (the Reynolds numbers decreasing from above about 3,000 to below about 2,000). In those tests, from about 7 to 10 minutes were used at each flow rate in order to measure the corresponding corrosion rate.

In the above tests, the corrosion was caused by a single phase aqueous liquid. But, consistent results have been obtained regarding the corrosion caused by a dispersed aqueous phase contained within an innocuous continuous phase. In the latter tests, the corrosion rates measured on a disc which was rotating at various speeds demonstrated that corrosion by a disperse phase is strongly influenced by the rotational speed. This corresponds with the general recognition that corrosion by dispersed aqueous phase depends on flow, interfacial, aqueous, electrochemical and metallic variables. The flow variables include velocity, flow geometry and the amount of dispersed water. The interfacial variables include interfacial tension and contact angle. The metal and aqueous variables are primarily controlled by the composition of the metal and the aqueous phase fluid.

Thus, it is now apparent that inserting a probe body, or making substantially any change in the generally uniform interior of a fluid-conveying conduit, any strongly influence the amount of turbulence in that region. Because of this, the present type of probes are uniquely advantageous in measuring the corrosion rate that is occurring within a conduit while the conduit is conveying a fluid at flow conditions which substantially duplicate those which predominate throughout the conduit.

LOW CORROSION RATES

Experiments were conducted to measure the lower limit of sensitivity of a system using probes of the present type. Some of the tests used only nitrogen gas in the sensor tube, others used nitrogen-purged deionized water, and still others used a pH-adjusted deionized water. In order to achieve a "no corrosion" state, tests were made during periods ranging from 14 to 159 hours. Typical test results are listed in Table 1.

TABLE 1

| RESULTS OF LOW CORROSION RATE STUDIES | | | | |
|---|---|---|---|---|
| SOLUTION | TEST LENGTH (HRS.) | SLOPE (μv/hr) | STD. ERROR (μv/hr) | CALCULATED C.R., (mpy) |
| N₂ ONLY | 138 | 0.00023* | — | 0.05 |
| N₂ PURGED DIW | 32 | 0.00002* | 0.00012 (0.3 mpy) | 0.005 |
| N₂ PURGED DIW | 20 | 0.00028* | 0.00015 (.03 mpy) | 0.06 |
| N₂ ONLY | 63 | −0.00016* | 0.00009 (.02 mpy) | −0.04 |
| N₂ PURGED pH 8 to 10 (NaOH) DISTILLED WATER | 138 | 0.0060* | — | 1.4 |
| N₂ ONLY | 14 | ≦0.00011* | — | ≦0.02 |
| N₂ ONLY | 37 | ≦0.00037** | — | ≦0.09 |
| N₂ ONLY | 87 | ≦0.00024 | — | ≦0.10 |
| N₂ ONLY | 72 | ≦0.00028 | — | ≦0.12 |
| pH 10.5 DIW | 159 | 0.00019 | — | 0.08 |

DIW = DEIONIZED WATER
*1.0 amp rms excitation
**17.5 Hz excitation

Regarding the data in Table 1, the actual corrosion rates were not verifiable in magnitude by weight loss since 0.1 mil per year is equivalent to only 8 milligrams per hour. However, in a few cases, weight measurements did verify that slow weight loss was occurring. The indicated corrosion rates were based on the resistance readings. The indicated standard slope errors were obtained by regression analysis performed on three sets of the data. The tests indicate that, with the present type of corrosion measuring probes, measurements can be made of rates as low as about 0.1 mpy.

PARTICULARLY PREFERRED EMBODIMENT

Laboratory tests of the type described above were also conducted on an embodiment of the present type of sensing element comprising a six-foot length of 4½ inch diameter pipe. That sensing element was the 72 inch length of 4½ inch outer diameter carbon steel pipe (composition including carbon 0.19%, manganese 0.59%, chromium 0.06%, molybdenum 0.5% and phosphorous 0.006%) with a nominal 0.150 inch wall thickness. A 34.5 inch subsection set in 1.5 inch from one end was machined down to half its original thickness. Three copper electrodes measuring 2 inches at the base were silver soldered to the pipe, one at the middle and one each at locations 1.5 inches in from the ends. Those electrodes provided a means for cable and wire attachments and defined the active zones of the sensing element. The sensing element was employed in conjunction with a balanced bridge resistivity measuring system, substantially as described above.

Calculations were made with respect to the effect of scaling up of the diameter and wall thicknesses on the sensitivity of the present type or corrosion measuring conduit sections. A formula was developed relating the Wheatstone bridge signal change ($\Delta E$), to metal loss ($X$), bridge voltage ($V$), cross-sectional wall areas ($A_2$-thick, $A_1$-thin), and diameter ($d$-outside, $d_2$-inside thick, $d_1$-inside thin). Equal lengths are assumed for thin and thick sections, and do not otherwise enter into the formula; however, for a given applied current, V is greater for longer lengths, and hence the sensitivity is higher, but not as a percentage of the impressed bridge voltage. The formula is:

$$\Delta E = Vx\pi \left[ \frac{A_2 d_1 - A_1 d_2}{(A_1 + A_2)(A_1 + A_2 - \pi x (d_1 + d_2))} \right]$$

For very small x; this reduces to:

$$\Delta E = Vx\pi \left[ \frac{A_2 d_1 - A_1 d_2}{(A_1 + A_2)^2} \right]$$

The reason for assuming constant outside diameter is for the use of two pipe sections of the same nominal diameter but of different schedules, as might be done to construct the probes to be used in a field location. Required sensitivity ($\Delta E/x$) is set as a constraint to see what V is required to achieve that sensitivity. Once V is known, the lengths required for various reasonable current levels are easily calculated from conventional formulas. The device shown in FIG. 1 has a sensitivity of $2 \times 10^{-5}$ volts/mil (volts per thousandth of an inch loss of metal thickness), and we can see that a sensitivity on this order would require a current of ten amps and lengths on the order of one hundred feet or more. Longer lengths are increasingly impractical, as are higher currents. In many situations, however, somewhat lower sensitivities can be tolerated due to the greater than 0.1 mil per year corrosion rates expected.

The response to the metal loss of the 4.5 inch device has been calculated theoretically for constant voltage—V, and constant current—i, excitation of the bridge. Constant V operation is preferred for linearity after balancing. But, for small losses after balancing, say, 2 or 3 mil, constant i is satisfactory and is much easier to implement due to the low bridge voltage of about 10 mv.

Metal loss subsequent to bridge balancing, and temperature variations both affect sensitivity. This effect is different from temperature-caused drift. Calculations show identical thin and thick section lengths and 2:1 wall thickness provide best temperature drift compensation when the bridge is balanced. A loss of 1 mil from the present corrosion measuring pipe section leaves the response linear, but greater losses lead to rising sensitivities, as do increasing temperatures, at the rate of about 1.5%/°C.

In selecting an operating frequency, it is essential to consider the skin-effect, or tendency for AC current to flow at the inside and outside edges of the wall. The skin-effect ratio is the AC to DC resistance; t/d is the wall thickness to diameter ratio, and f is the frequency.

For the present measuring elements, the skin-effect ratios may be determined and the AC resistance ratios of the thin and thick sections may be calculated. For example, a 2:1 resistance ratio at 5 Hz, is the same as at DC; but, the two sections have almost equal resistances (1.3:1) at 35 Hz, and at this frequency most sensitivity would be lost, if the device worked at all. Actual measurements of iR drops in the two sections have been performed at several frequencies. The results agree fairly well with the estimates.

The uniformity of current flow in the present corrosion measuring pipe has been determined by making local iR drop readings around and along the pipe with a hand-held pickup using two pointed electrodes one inch apart. The end readings indicate poor uniformity near the current supplying connections, however, the other readings show excellent distribution (better than ±7%) throughout the central two-thirds of the pipe.

The direction of signal change to be expected from corrosion can be readily determined by jumpering the thin and thick sections with test leads. Corrosion causes a faster rise in resistance of the thin section, and this can be simulated by reducing the resistance of the thick section or paralleling it with a jumper wire. The spike so obtained is in the (+) direction, and corrosion caused signal slopes should therefore have (+) polarities.

Five sets of experiments have been conducted with the above-described 4.5 inch corrosion measuring, as indicated in Table 2. The first experiment involved a long period of near zero corrosion, with the pipe sealed and full of $N_2$ gas (also, the exterior coated with a corrosion inhibiting paper). The remaining tests were each started with thirty liters of deionized water in the measuring pipe/reservoir system (always pH adjusted to $\simeq 10$ with NaOH, $N_2$ purged, and initially flowing—in all but one test). Next, hydrochloric acid was added to the water in the system and recordings were made for the time indicated. Titrations of acid samples with caustic were performed periodically to provide additional corrosion rate data, and these are presented in Table 2 along with polarization resistance corrosion rates, corrosometer signal slopes obtained by regression analysis, standard slope errors, and calculated sensitivities based on the titrations.

TABLE 2

SUMMARY DATA
All Solutions $N_2$ Purged   Solution Volume = 30 Liters
Current = 8.7–9.3 AMPS   Flow = 3.7 Liters/Minute

| Expt. No. | System | Time (Hours) | Corrosion Rate (MPY) By Titration | Corrosion Rate (MPY) By Pol. Res. | Average Slope ($\mu v$/Hour) | Standard Slope Error ($\mu v$/Hr.) | Sensitivity ($\mu v$/Mil) Based on Titr.C.R. |
|---|---|---|---|---|---|---|---|
| 1 | $N_2$, Sealed | 65 | — | — | 0.0040 | 0.0006 | — |
| 2 | Deionized Water* | 94 | — | 0.6 | 0.0004 | 0.0001 | — |
|   | 0.51% HCl Added | 25 | 152 | 53–190 | 0.0189 | 0.0003 | 1.07 |
| 3 | Deionized Water* | 65 | — | 0.6 | 0.0005 | — | — |
|   | 0.51% HCl Added | 18 | 48 | 11–24 | 0.0089 | 0.0005 | 1.70 |
|   | Expended Solution | 54 | — | — | 0.0001 | 0.0001 | — |
| 4 | Deionized Water*, No Flow | 19 | — | — | 0.0021 | 0.0003 | — |
|   | Deionized Water* | 72 | — | — | 0.0003 | 0.0001 | — |
|   | 1.0% HCl Added | 4 | 85 | 140–320 | 0.034 | 0.0022 | — |
|   | 0.0038% Rodine-213 Added | First 7 | ~42 | 27–200 | 0.030 | — | Net = 5.3 |
|   | (Same) | Next 13 | ~12 | 25–95 | 0.0009 | 0.0005 | — |
| 5 | Deionized Water* | 17 | — | — | 0.0017 | 0.0003 | — |
|   | 1.0% HCl Added | First 7 | 0 | 35–125** | −0.0005 | 0.0005 | — |
|   | (Same) | Next 44 | 28 | 34–142** | 0.0036 | 0.0002 | 1.11 | avg. = 2.3 $\mu v$/mil

*pH ~ 10
**Suspect Values

As indicated in Table 2, the final corrosion rates (measured by polarization resistance) are suspect. They are probably due to material being trapped under the electrodes.

The slopes in the no-corrosion cases are all positive and range from 0.0003 to 0.004 $\mu v$/hour, although the greatest drifts occur during no-flow periods ($N_2$ sealed;

and deionized water, no-flow), when temperature differences between the thin and thick sections may be significant. Some of this slow drift is due to corrosion, as corrosion cannot be completely arrested. A slope of 0.004 μv/hr is equivalent to 15 mpy using the average sensitivity of 2.3 μv/mil. Some of this is instrument drift, but probably does not amount to more than 2-4 mpy.

In Table 2, the 0.0189 μv/hr slope given for experiment #2 represents a 25 hour average, but it is apparent that 3 hours would have been adequate to obtain a slope value. Experiment #3 illustrates a period of near zero corrosion (DIW), then high corrosion (0.051% HCl), then low corrosion again once the acid is consumed. Experiment 190 4 demonstrates the delayed onset of corrosion, apparently due to residual inhibitor left from the previous experiment. Leakage began at a seam in the top center of the pipe during experiment #5. In all reported tests and other less than 10 mils of metal had been removed, however, some isolated pitting and grooving led to this failure in an area which still measured 0.076 inch thick by ultrasonics.

The average sensitivity shown in Table 2 is 2.3 μv/mil, which is somewhat less than the 5 μv/mil predicted. This discrepancy and the variation in the sensitivities may be due to errors in the titration and linear polarization corrosion rate measurements, and/or unusual resistance effects arising from non-uniform corrosion. The lower limit of sensitivity is established by the drift rate in the absence of corrosion, which has run as high as 0.004 μv/hr, or 15 mpy. The approximate time required to make a measurement depends on the corrosion rate. Temperature effect on baseline stability was tested during a very slow cooling of flowing deionized water. Rapid liquid temperature changes and a slow flow rate may lead to large signal disturbances caused by imbalance of thick and thin section temperatures.

Various use situations, such as a buried pipe, are less likely to have such a temperature-induced imbalance due to the much higher flow rates and the stabilizing influence of the soil or other surroundings. We, therefore, tested slow temperature changes to imitate an in-service pipe and measured a sensitivity of 0.006 mil/°F. Large spikes accompany temperature changes of the flowing medium, but these are due to lag in equilibration of the relatively thick and thin pipe sections.

Figure 4:
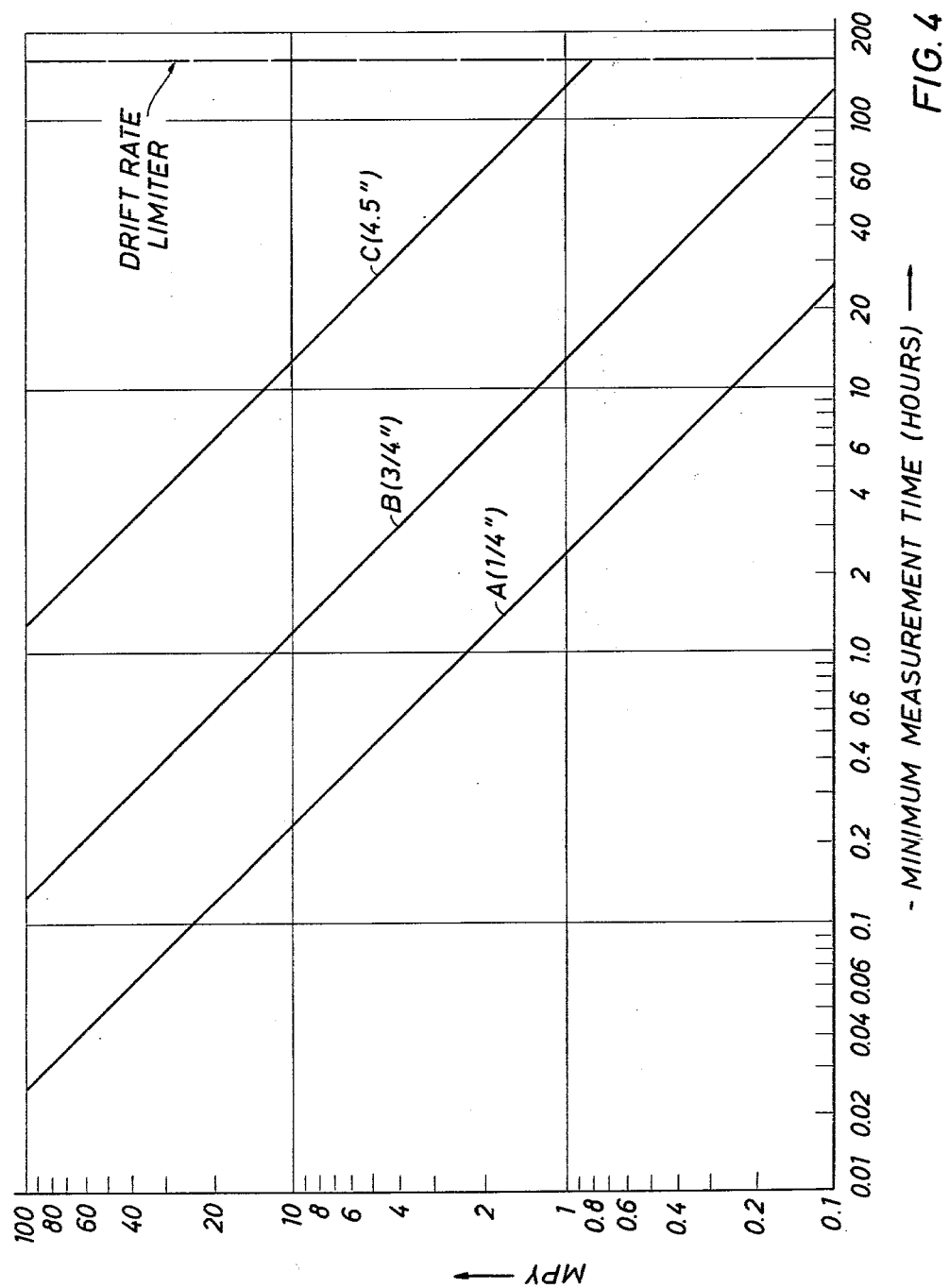
FIG. 4 shows a graph of the minimum measuring time needed for measuring different corrosion rates with different embodiments of the present type of measuring probe.

In a corrosion measuring conduit of the present type, the tube diameter, length, wall thicknesses, and current all affect the sensitivity, and the time required to perform a measurement at any given corrosion rate. FIG. 4 shows a graph of the time-to-measure requirements for variously sized measuring conduits. Curve A relates to the 4.5 inch diameter pipe element described above. Curve B relates to a ¾ inch diameter element 36 inches long with 0.085 and 0.042 inch wall thicknesses, and, Curve C relates to ¼ inch diameter element which is 4 inches long with 0.010 and 0.024 inch wall thickness. These and practical elements for consideration, and two, A and C have been built and tested. Tests of two of these have shown that the "zero corrosion" drift rates, which ultimately limits sensitivity, are typically 0.0002 to 0.0005 μv/hr, despite differences in currents and sensitivities.

It is assumed that in order to be measured, the corrosion rate signal change must exceed the drift rate, and further, the minimum signal change must be 0.07 μv (based on graphical analysis) in order to calculate a corrosion rate. These values and the theoretical sensitivities (at currents of 1-10 amps) for each tube were used to plot FIG. 4. Tube B could be used, for example, in a heat exchanger where corrosion rates of 2 to 20 mpy are typical. From FIG. 4, it can be seen that a period of 0.6 to 6 hours could be required for the measurement. These values are only approximate, but may be used to ascertain which measuring conduit is best suited for a particular application.

What is claimed is:

1. A process of measuring the rate of corrosion within a fluid-conveying metallic pipe comprising:
   utilizing as a portion of said fluid-conveying pipe a corrosion measuring section which is made of substantially the same metal and has an interior configuration that is typical of the fluid-containing pipe, but contains a pair of relatively thick and thin wall sections which are electrically connected as the arms of an electrical resistance measuring bridge circuit; and,
   measuring the ratio between the resistances of said relatively thick and thin wall sections at least two times in order to determine the rate at which corrosion is occuring within the fluid conveying pipe.

2. A method of measuring the corrosion of a metallic conduit which conveys or is contacted by a corrosive fluid, comprising:
   making of modifying a section of metallic circuit to provide a measuring section in which (a) in locations contacted by said corrosive fluid, both the composition and configuration of the metal in the measuring section are substantially the same as those predominating throughout said metallic conduit; and, (b) in locations not contacted by said corrosive fluid, the thickness of the metal in one portion of the measuring section is thin relative to that in another portion; and, (c) said relatively thick and thin portions of the measuring section are connected to means for employing them as the arms of an electrical resistance measuring bridge; and,
   connecting said measuring section into said metallic conduit to convey or be contacted by at least some of said corrosive fluid.

3. The process of claims 1 or 2 in which the fluid-conveying pipe or conduit in which the rate of corrosion is measured is a fluid-transporting pipeline.

4. The process of claims 1 or 2 in which the fluid-conveying pipe or conduit in which the rate of corrosion is measured is a component of a heat exchanger.

5. A corrosion measuring conduit section capable of being connected into an electrically conductive fluid-confining conduit having a corrodible wall which is in contact with the corrosive fluid, comprising:
   a measuring conduit section in which (a) in locations capable of being contacted by said corrosive fluid, both the composition and configuration of the metal in said measuring conduit section are substantially the same as those which predominate throughout said fluid-confining conduit; (b) in locations within said measuring conduit section that do not contact the corrosive fluid, the thickness of the wall in one portion is thin relative to that in another portion; and, (c) said relatively thick and thin wall portions of the conduit section contain portions capable of receiving means for electrically connected said wall portions as the arms of an electrical resistance measuring bridge; and, means for mechanically connecting said measuring conduit section into said fluid-confining conduit.

6. The measuring conduit section of claim 5 in which that section and said fluid-confining conduit are composed of carbon steel.

7. The measuring conduit section of claim 5 or 6 in which said leads for electrically connecting the thick and thin wall portions into a resistance measuring bridge are soldered directly onto those wall portions.

* * * * *